United States Patent [19]

Aude et al.

[11] 4,290,973

[45] Sep. 22, 1981

[54] PROCESS FOR MANUFACTURING PETROLEUM SULFONATES AND THE RESULTANT PRODUCTS

[75] Inventors: Robert Aude, Biviers; Pierre Baumgartner, Grenoble; Jean-Pierre Desmarquest, Mesnil Le Roi; Jean-Pierre Franck, Bougival, all of France

[73] Assignee: Institut Francais du Petrole, Rueil-Malmaison, France

[21] Appl. No.: 141,246

[22] Filed: Apr. 17, 1980

[30] Foreign Application Priority Data

Apr. 17, 1979 [FR] France .................................. 79 09830

[51] Int. Cl.$^3$ ............................................. C07C 143/24
[52] U.S. Cl. .................................................. 260/505 R
[58] Field of Search ............. 260/505 R, 504 R, 505 S

[56] References Cited

U.S. PATENT DOCUMENTS

| | | | |
|---|---|---|---|
| 2,865,849 | 12/1958 | van Loon et al. | 208/211 |
| 3,254,714 | 6/1966 | Gogarty et al. | 166/274 |
| 3,302,713 | 2/1967 | Ahearn et al. | 166/274 |
| 3,373,808 | 3/1968 | Patton | 166/275 |
| 3,497,006 | 2/1970 | Jones et al. | 166/273 |
| 3,506,071 | 4/1970 | Jones | 166/273 |
| 3,956,372 | 5/1976 | Coleman, Jr. et al. | 260/505 S |

FOREIGN PATENT DOCUMENTS 1200109 12/1959 France .
 928548 6/1963 United Kingdom .
1275005 5/1972 United Kingdom .

*Primary Examiner*—Alan Siegel
*Attorney, Agent, or Firm*—Millen & White

[57] ABSTRACT

Petroleum sulfonates are manufactured by reacting a hydrocarbon stock with a sulfonating agent and neutralizing the sulfonation product. The hydrocarbon stock is pretreated with hydrogen, in the presence of a NiW or NiMo catalyst, under specified conditions: its sulfur content is decreased by at least 50%, but its aromatic hydrocarbon content is decreased by not more than 35%, so that the aromatic hydrocarbons content remains at least 20% b.w. after completion of the pretreatment.

27 Claims, No Drawings

PROCESS FOR MANUFACTURING PETROLEUM SULFONATES AND THE RESULTANT PRODUCTS

BACKGROUND OF THE INVENTION

This invention concerns the manufacture of petroleum sulfonates which can particularly be used to confer micellar properties to mixtures of hydrocarbons with water. These products have found a particular use in the manufacture of microemulsions which can be used in the assisted oil recovery.

The petroleum sulfonates are surfactive agents obtained by sulfonation of crude oils or oil fractions obtained by distillation.

The oil bases which can be used according to the process of the invention may be vacuum distillation cuts, particularly those used in the production of lubricating oils, or optionally dewaxed deasphalted distillation residues, for example, a heavy oil known as Bright Stock.

U.S. Pat. No. 3,254,714 discloses the use of microemulsions comprising a petroleum sulfonate for recovering crude oil from underground formations.

U.S. Pat. No. 3,497,006 discloses the use of water-in-oil micellar dispersions having a high water content, i.e. 55 to 90%, to recover the crude oil, the micellar dispersion consisting of a petroleum sulfonate having an average molecular weight of about 350 to 520.

U.S. Pat. No. 3,506,071 discloses the recovery of oil by injecting micellar dispersions whose dispersion phase is water, which preferably consist of a petroleum sulfonate having an average molecular weight of 350 to 520.

U.S. Pat. No. 3,302,713 discloses the injection of an aqueous solution comprising a petroleum sulfonate having an average molecular weight of 450 to 500, which is obtained by sulfonating a hydrocarbon having a boiling range of 371° to 593° C. with gaseous SO$_3$.

U.S. Pat. No. 3,373,808 discloses the injection of water containing sulfonates obtained by sulfonating a hydrocarbon having a boiling range of 260° to 816° C. and an average molecular weight of 250 to 700 with gaseous or liquid SO$_3$; it is specified that polysulfonation results from raising the reaction temperature and increasing the molar ratio of the sulfonation agent.

U.S. Pat. No. 3,956,372 discloses the manufacture of petroleum sulfonates by sulfonation of a hydrocarbon raw material consisting of gas oil having an average molecular weight of 250 to 700 and containing at least 20% of aromatic constituents with a solution of SO$_3$ in 1,2-dichlorethane.

SUMMARY OF THE INVENTION

It has now been found that petroleum sulfonates having a high content of active material can be manufactured by using a hydrocarbon raw material whose aptitude to sulfonation has been increased by a treatment with hydrogen in the presence of NiW or NiMo catalyst.

DETAILED DISCUSSION

The starting hydrocarbon material which is used in the process of the invention is a heavy oil fraction having an average molecular weight of at least 250. It may consist of a distillate having an average molecular weight of about 250 to 700 and preferably 250 to 500, or a deasphalted distillation residue (dewaxed or not), for example that which is used as base in the manufacture of Bright Stock.

The aromatic constituents content of the raw material must amount to at least 20%, or better at least 25%, and preferably 40 to 60% by weight. Before sulfonation, the oil cut is subjected, according to the invention, to controlled hydrogenation, in order to decrease the sulfur content by at least 50% without decreasing the aromatic hydrocarbon content by more than 35%, said content remaining at least 20% by weight. Although the mechanism is not fully known, it seems that the hydrogenation concerns particularly the poly-aromatic hydrocarbons. There is no upper limit for the decrease of the sulfur content; however economical aspects and the necessity to simultaneously limit the decrease of the aromatics content may limit this decrease.

A preferred catalyst to attain these objects comprises at least one nickel and/or cobalt compound and at least one molybdenum and/or tungsten compound incorporated to (or deposited on) a carrier, preferably an alumina carrier, the ratio $$R = \frac{\text{Ni and/or Co}}{\text{W and/or Mo}},$$

where the metal proportions are expressed as gram-atoms of metal, being from 0.1:1 to 1:1, preferably from 0.25:1 to 0.6:1. Useful catalysts, which are given as examples, contain the NiW, NiMo or CoMo metal pairs, the preferred pair being NiW. The aggregate content of the catalyst metals is usually between 5 and 50% by weight (as metal).

Alumina of low acidity is a preferred carrier. A carrier of low acidity or without acidity has an ammonia adsorption neutralization heat preferably lower than 10 calories per gram of alumina at 320° C. and a pressure of 300 mm mercury; limited acidity of the carrier can however be tolerated without serious inconvenience. The acidity of the carrier may be determined by the known test of ammonia adsorption as described, for example, in Journal of Catalysis 2, 211–222 (1963).

Alumina to be used as carrier for the above catalysts may be obtained, for example, by calcining tetragonal boehmite. The physical characteristics of these carriers are preferably the following: a specific surface between 10 and 300 m$^2$/g, preferably between 50 and 200 m$^2$/g, a total pore volume between 0.1 and 1 cc/g, preferably between 0.3 and 0.8 cc/g, an average diameter of the pores between 50 and 1000 Å and preferably between 80 and 500 Å.

The catalysts may be prepared in conventional manner, for example, by incorporation or impregnation of the carrier with compounds of the above metals, drying and calcining, so as to convert said compounds to oxides. After completion of this preparation, the catalytic metals are usually present as oxides in the catalyst; it is however preferably operated with the same metals in the sulfided state. Sulfiding may be effected before starting the hydrotreatment plant, for example by passing a mixture of H$_2$ with H$_2$S; sulfiding may also be effected with the charge, at the beginning or in the course of the operation, or by any other means known to the specialists.

The operating conditions of the hydrogenation treatment according to the process of the invention are usefully the following:

the total pressure is between 10 and 200 bars and preferably between 30 and 150 bars, the temperature is between 200° and 450° C. and preferably between 325° and 425° C., the amount of hydrogen injected with the charge is usefully proportional to the chemical consumption of hydrogen; it is usually at least 20 Nm3/m3, for example about 20 to 150 Nm3/m3 of the liquid charge, the gas recycle rate, expressed as the ratio of $H_2$ to the liquid hydrocarbons is usually between 100 and 2000 Nm3/m3, for example, between 400 and 800 Nm3/m3, the space velocity (VVH) ranges from 0.1 to 5 m$^3$ of the treated liquid charge/m$^3$ of catalyst/hour, and preferably from 0.5 to 3.

The main advantages of this hydrotreatment which precedes the sulfonation are:

the removal of the sulfur compounds, the nitrogen compounds and the poly-aromatic compounds which generate tar in the sulfonation step, the possibility to adjust the hydrogenation level to obtain a petroleum sulfonate having as high a content of active material as possible, the adaptability to quite diverse particular cuts.

In the sulfonation step of the process according to the invention, $SO_3$ is preferably used as the sulfonation agent for the hydrotreated bases, since it reacts quantitatively with the aromatic molecules without forming by-products.

As the sulfonation reaction is rapid and highly exothermic ($\Delta H = -40$ Kcal/mol $SO_3$), $SO_3$ is preferably used in the dilute state, either in a solvent or in an inert gas.

When using a solvent, the dilution molar ratio of $SO_3$ to the solvent is usually selected from 0.01 to 2, preferably from 0.2 to 1, specially from 0.25 to 0.5. Such solvents as 1,2-dichlorethane, trichlorethylene, nitrobenzene, nitropropane or any other solvent inert to $SO_3$ may be used with advantage.

In the case of oils of low viscosity, the sulfonation may be effected without solvent. $SO_3$ is then introduced in the gas phase in dilute condition. The preferred gaseous diluents are air, nitrogen, $SO_2$ or any other inert gas. The concentration of $SO_3$ in the gas mixture may range from 1 to 50%, preferably from 5 to 20%, particularly from 7 to 15% by volume. The amount of $SO_3$ to be used is advantageously from about 0.04 to about 0.3, preferably 0.08 to 0.25 and quite particularly from 0.1 to 0.2 kg/kg of oil material to be sulfonated.

Satisfactory homogenization may be obtained by reacting $SO_3$ with the oil, either in turbulent flow in a tubular reactor with a falling film or in a reactor having a mechanically stirred film.

The conditions of the reaction are not critical. The reaction temperatures are normally in the range from 0° to 120° C., preferably 45° to 100° C., particularly 50° to 70° C. The pressures are in the range from 0.01 to 150 bars, preferably 0.15 to 75, and particularly 0.2 to 5 bars. The residence time may range from 0.001 to 3600 sec., preferably 0.01 to 360, particularly 0.02 to 60 sec.

At the exit from the reactor, the sulfonation products may optionally be fractionated. The solvent may be distilled or steamstripped. The sulfonic acids may be neutralized, either with gaseous ammonia or with a solution of a base, preferably a solution of sodium hydroxide or ammonia in water or in a mixture of water with alcohol. The pH of the neutralized reaction products is preferably from 5 to 9.

The neutralized mixture consists of two phases. The upper phase contains the heavy sulfonates and the unreacted oil. The lower aqueous phase (or water-alcohol phase), which contains sulfates and salts of light sulfonic acids, is separated by decantation.

The upper phase, which contains the heavy petroleum sulfonates, may be made more concentrated in active material by an extraction with an aqueous alcohol. The aqueous alcohol may be aqueous methanol, ethanol, n-propanol, n-butanol, iso-butanol or tert. butanol. Aqueous isopropanol is preferred. The composition of the extraction solvent is preferably 50 to 80% and particularly 55 to 75% alcohol (for example isopropanol), the remainder being water. The addition of the extraction solvent usually results in the formation of 2 or 3 phases. In the case of 3 phases, the upper phase consists of unsulfonated hydrocarbons; the intermediate phase contains the petroleum sulfonate dissolved in the alcohol; and the lower phase consists of sulfate and sulfite of the base which has been used for the neutralization. Only two phases may be present, the intermediate phase being then present in admixture with either the upper phase or the lower phase.

The alcoholic sulfonate extract may usefully constitute the base solution for the manufacture of the micro-emulsion. The selected alcohol is then the co-surfactant. A concentrate of active material may be obtained by evaporation in vacuo of the extraction alcohol.

The sulfonation yield of a petroleum base is defined as the amount of surface-active material obtained per 100 g of starting material. This amount of suface-active material is determined by the usual method with hyamine (method NF T 73.258).

The compounds whose active material content is between 20 and 80% and preferably between 30 and 70% may be advantageously used for manufacturing micro-emulsions adapted to the assisted oil recovery.

The examples given hereunder show the influence of a hydrogenation treatment applied to the base oils on the amount of sulfonates obtained from a given oil cut. The examples 1, 3, 6 and 8 are given for comparison.

EXAMPLE 1 (comparison example)

A petroleum sulfonate is prepared from a deasphalted vacuum distillation residue of a Kuwait oil. Its characteristics are the following:

| | |
|---|---|
| $d_4^{15}$ | 0.930 |
| % S by weight | 2.73 |
| % Aromatics by weight | 50.0 |
| Average molecular weight | 600 |

The sulfonation agent is a solution of 20% b.w. $SO_3$ in 1,2-dichlorethane. The sulfonation is effected in a 1 liter glass reactor provided with a jacket and an efficient stirrer and maintained at 40° C.

The oil is dissolved into 1,2-dichlorethane directly in the reactor and the $SO_3$ solution is injected with a metering pump at a rate of 500 cc/h. $SO_3$ is injected in an amount of 0.15 kg/kg of oil.

When the injection is achieved, stirring and temperature are maintained for half an hour.

The reaction product is neutralized with a 20% b.w. sodium hydroxide solution in a mixture of 50 parts water and 50 parts isopropanol by volume up to a pH of 9–10.

The temperature is maintained above 30° C. during the neutralization. The lower water-alcohol phase is eliminated by decantation.

The upper phase is treated as follows: the solvents are removed at 110° C. in a rotative evaporator, under vacuum of the water pump.

Drying is followed with azeotropic stripping of water with xylene. The content of sulfonated active material, determined with hyamine, is 12.6% b.w.

EXAMPLE 2

There is used the same deasphalted vacuum distillation residue from Kuwait; however it is subjected to a hydrogen treatment before sulfonation, as follows:

catalyst: $NiW/Al_2O_3$
  NiO: 3.8% b.w.
  $WO_3$: 25.7% b.w.
  $Al_2O_3$: 70.5% b.w.
  Surface: 180 m²/g  Pore volume: 0.4 cc/g The catalyst has been presulfided at 320° C. under atmospheric pressure with a gas containing 1.5% by volume of $H_2S$ in hydrogen.

Operating conditions:
  Total pressure ($P_T$): 125 bars
  Temperature: 350° C.
  VVH: 1 m3/m3/h
  $H_2/HC$: 600 Nm3/m3

The properties of the charge and the product are the following:

|  | Charge | Product |
|---|---|---|
| $d_4^{15}$ | 0.930 | 0.900 |
| % S by weight | 2.73 | 0.39 |
| N ppm by weight | 900 | 320 |
| $\eta_D^{70}$ | 1.4978 | 1.4852 |
| viscosity at 98.9° C. (cSt) | 33.94 | 22.30 |
| aniline point °C. | 102.3 | 113.4 |
| % Aromatics b.w. | 50.0 | 44.8 |

The sulfonation is identical in all aspects to that of example 1.

The amount of sulfonated active material, determined with hyamine, is 22.4% b.w.

EXAMPLES 3 TO 5

An oil cut obtained by distillation of a Kuwait crude oil has been subjected to hydrotreatments of increasing severity to define an optimal hydrotreatment rate.

The sulfonation is effected with $SO_3$ dissolved in 1,2-dichlorethane at 60° C. The $SO_3$ injection rate is 0.230 kg/kg of oil. The other conditions are as in example 1.

Example 3 relates to the sulfonation of un-hydrotreated oil. The examples 4 and 5 relate to the sulfonation of the oil hydrotreated at different severity degrees.

for example 4: $P_T=40$ bars, T=350° C., VVH=2, $H_2/HC=300$ Nm3/m3.
  for example 5: $P_T=125$ bars, T=350° C., VVH=2, $H_2/HC=430$ Nm3/m3.

| | | BASE PRODUCT | | SULFONATED PRODUCT |
|---|---|---|---|---|
| EXAMPLE | MOL. WEIGHT | AROMATICS CONTENT (% b.w.) | SULFUR* CONTENT (% b.w.) | ACTIVE MATERIAL CONTENT (% b.w.) |
| 3 | 350 | 48.6 | 2.55 | 2.7 |
| 4 | 350 | 47.4 | 0.62 | 31.4 |
| 5 | 350 | 42 | 0.53 | 21.6 |

*ASTM D 2549

It is seen that the best sulfonated product is that of example 4.

EXAMPLES 6 AND 7

The same proceedings as in the examples 3 to 5 have been followed, however from a petroleum cut obtained by distillation of an Iraq crude. Example 6 corresponds to the sulfonation of the unhydrotreated base as follows. Example 7 corresponds to the sulfonation of hydrotreated base as follows:

$P_T=80$ bars, T=350° C., VVH=1, $H_2/HC=600$ Nm3/m3.

The conditions of the sulfonation are the same as used in the above examples 3 to 5.

| | | BASE PRODUCT | | SULFONATED PRODUCT |
|---|---|---|---|---|
| EXAMPLE | MOL. WEIGHT | AROMATICS CONTENT (% b.w.) | SULFUR CONTENT (% b.w.) | ACTIVE MATERIAL CONTENT (% b.w.) |
| 6 | 300 | 42.5 | 2.5 | 2.5 |
| 7 | 300 | 36.7 | 0.48 | 41.7 |

EXAMPLES 8 TO 10

The same experiments have been effected with another oil distillation cut from an Iraq crude.

Example 8 relates to the sulfonation of the un-hydrotreated cut. The hydrotreatment conditions for the examples 9 and 10 are:

EXAMPLE 9

$P_T=40$ bars, T=350° C., VVH=2, $H_2/HC=600$ Nm3/m3.

EXAMPLE 10

$P_T=80$ bars, T=350° C., VVH=1, $H_2/HC=600$ Nm3/m3.

The sulfonation is effected in the same conditions as in the above examples 3 to 7. The $SO_3$ injection rate is 0.180 kg/kg of oil.

| EXAMPLE | MOL. WEIGHT | BASE PRODUCT | | SULFONATED PRODUCT |
| --- | --- | --- | --- | --- |
| | | AROMATICS CONTENT (% b.w.) | SULFUR CONTENT (% b.w.) | ACTIVE MATERIAL CONTENT (% b.w.) |
| 8 | 450 | 45.8 | 2.6 | 3 |
| 9 | 450 | 43.5 | 1.2 | 14.4 |
| 10 | 450 | 42.2 | 0.75 | 36 |

EXAMPLE 11

This example relates to a continuous sulfonation operated in a reactor with a mechanically stirred film, by means of gaseous $SO_3$ diluted in dry air.

The charge is the same hydrotreated petroleum cut as obtained in example 9.

The sulfonation conditions are:
Feed rate of the charge: 0.65 l/h, thus 0.58 mol. aromatics per hour.
Feed rate of $SO_3$: 15 l/h, corresponding to 0.58 mol/h.
Feed rate of dry air: 325 l/h
Concentration of $SO_3$ in the gas mixture: 5% by vol.
Molar ratio of $SO_3$ to the aromatics: 1
Residence time in the reactor: 5 mn
$SO_3$ is fully converted.

At the exit of the reactor, the sulfonated product is neutralized in continuous manner with 30% aqueous sodium hydroxide. After evaporation of water at 120° C. in vacuo, the resultant sulfonate has a 38% by weight content of surface-active material.

What we claim is:

1. A process for manufacturing petroleum sulfonates, which comprises the steps of:
   (a) treating a hydrocarbon charge, having an aromatic hydrocarbon content of at least 20% by weight and an average molecular weight of at least 250, by contacting said charge with hydrogen in the presence of a carrier-supported NiW or NiMo hydrogenation catalyst having a Ni/W or Ni/Mo ratio, expressed as gram-atoms of the metals, of from 0.1:1 to 1:1, at a temperature of from 200° to 450° C., a total pressure of from 10 to 200 bars and an amount of hydrogen of at least 20 $Nm^3$ per $m^3$ of said hydrocarbon charge, said treatment with hydrogen being so effected as to decrease the sulfur content by at least 50% without decreasing the aromatic hydrocarbons content by more than 35%, the latter remaining at least 20% by weight after said treatment;
   (b) reacting the hydrotreated effluent from step (a) with a sulfonating agent comprising $SO_3$; and
   (c) neutralizing the sulfonation product with a base and recovering the resultant neutralized sulfonated product.

2. A process according to claim 1, wherein the sulfonating agent in step (b) consists essentially of $SO_3$.

3. A process according to claim 2, wherein $SO_3$ is dissolved in an inert organic solvent.

4. A process according to claim 3, wherein said organic solvent is 1,2-dichloroethane, trichloroethane, nitrobenzene or nitropropane.

5. A process according to claim 3, wherein the molar ratio of $SO_3$ to solvent is from 0.01 to 2.

6. A process according to claim 5, wherein said molar ratio is from 0.2 to 1.

7. A process according to claim 5, wherein said molar ratio is from 0.25 to 0.5.

8. A process according to claim 2, wherein $SO_3$ is diluted with an inert gas.

9. A process according to claim 8, wherein said inert gas is air, nitrogen or $SO_2$.

10. A process according to claim 9, wherein the concentration of $SO_3$ in said inert gas is from 1 to 50% by volume.

11. A process according to claim 10, wherein said concentration is from 5 to 20% by volume.

12. A process according to claim 10, wherein said concentration is from 7 to 15% by volume.

13. A process according to claim 1, wherein the amount of $SO_3$ used in step (b) is from 0.04 to 0.3 kg per kg of said effluent from step (a).

14. A process according to claim 13, wherein said amount of $SO_3$ is from 0.08 to 0.25 kg per kg of effluent.

15. A process according to claim 14, wherein said amount is from 0.1 to 0.02 kg per kg of effluent.

16. A process according to claim 1, wherein sulfonation step (b) is effected at a temperature of from 0° to 120° C., a pressure of from 0.01 to 150 bars and a residence time of from 0.001 to 3600 seconds.

17. A process according to claim 1, wherein the sulfonation product is neutralized to a pH of from 5 to 9.

18. A process according to claim 1, wherein in step (c), said neutralized sulfonated product is recovered as an oily phase comprising sulfonates and unsulfonated oil; and wherein step (c) further comprises extracting said oily phase with an aqueous alcohol solution of from 50 to 80% of methanol, ethanol, n-propanol, isopropanol, n-butanol, isobutanol or tert-butanol in water, and recovering a phase comprising petroleum sulfonates and alcohol.

19. A process according to claim 1, wherein said catalyst in step (a) is in the sulfided state.

20. A process according to claim 1, wherein said hydrocarbon charge comprises from 40 to 60% by weight of aromatic hydrocarbons.

21. A process according to claim 1, wherein the total content of the active metals Ni and W or Mo of the catalyst is from 5 to 50% by weight, these metals being present in the sulfided state.

22. A process according to claim 1, wherein said Ni/W or Ni/Mo ratio is from 0.25:1 to 0.6:1.

23. A process according to claim 1, wherein the catalyst is a NiW catalyst.

24. A process according to claim 1, wherein the catalyst carrier is alumina of low acidity or devoid of acidity, corresponding to a neutralization heat by ammonia adsorption lower than 10 calories per gram of alumina at 320° C. under a 300 mm Hg pressure.

25. A process according to claim 1, wherein the catalyst carrier is an alumina carrier of specific surface between 50 and 200 $m^2/g$ and of pore volume between 0.3 and 0.8 $cm^3/g$.

26. A process according to claim 1, wherein in step (a) the hydrogenation temperature is from 325° to 425° C., the total pressure from 30 to 150 bars, the hydrogen amount injected with the charge from 20 to 150 Nm3/m3 of the liquid charge, the gas recycle rate from 100 to 2000 Nm3 hydrogen per m³ of the liquid charge and the space velocity (VVH) from 0.1 to 5 m³ of liquid charge per m³ of catalyst per hour.

27. The petroleum sulfonates obtained by a process according to claim 1.

* * * * *